US008786688B2

(12) United States Patent  (10) Patent No.: US 8,786,688 B2
Saito  (45) Date of Patent: Jul. 22, 2014

(54) ENDOSCOPE AND ENDOSCOPE SYSTEM

(75) Inventor: Saeri Saito, Sagamihara (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/587,063

(22) Filed: Aug. 16, 2012

(65) Prior Publication Data

US 2013/0038709 A1   Feb. 14, 2013

Related U.S. Application Data

(63) Continuation of application No. PCT/JP2011/073401, filed on Oct. 12, 2011.

(30) Foreign Application Priority Data

Oct. 14, 2010  (JP) .................................. 2010-231763

(51) Int. Cl.
*A61B 1/045*    (2006.01)

(52) U.S. Cl.
CPC ........................................ *A61B 1/045* (2013.01)
USPC ............................................................ 348/65

(58) Field of Classification Search
CPC .............. A61B 1/045; A61B 1/00009; A61B 1/00059; A61B 1/042; A61B 1/05; A61B 1/0638
USPC .............. 348/68–241; 382/128; 600/101–180
See application file for complete search history.

(56) References Cited

U.S. PATENT DOCUMENTS 5,374,953 A * 12/1994 Sasaki et al. ..................... 348/65
5,434,615 A *  7/1995 Matumoto ...................... 348/72
6,878,109 B2 *  4/2005 Yamaki et al. ................. 600/180
7,365,768 B1 *  4/2008 Ono et al. ......................... 348/76
7,585,272 B2 *  9/2009 Abe ................................. 600/101
7,944,466 B2 *  5/2011 Abe et al. ......................... 348/71
8,243,172 B2 *  8/2012 Usami et al. ................... 348/241

(Continued)

FOREIGN PATENT DOCUMENTS

JP     05-176883     7/1993
JP     06-105807     4/1994

(Continued)

OTHER PUBLICATIONS

European Search Report dated Apr. 18, 2013 from corresponding European Patent Application No. 11 83 2550.5.

*Primary Examiner* — William C Vaughn, Jr.
*Assistant Examiner* — Luis M Perez
(74) *Attorney, Agent, or Firm* — Scully, Scott, Murphy & Presser, P.C.

(57) ABSTRACT

An endoscope includes: a CDS circuit that samples an image pickup signal from a CCD via a feedthrough sampling pulse SHP and a clamp pulse SHD to output a post-sampling image pickup signal; a CPU that controls a sampling timing of each of SHP and SHD and evaluates the post-sampling image pickup signal from the CDS circuit, and a flash memory that stores timing information on the respective timings and timing determination procedure information. The CPU, upon receipt of an adjustment instruction for adjustment of the respective timings of SHP and SHD, rewrites the timing information in the flash memory according to a result of evaluation of a plurality of post-sampling image pickup signals obtained by shifting the respective timings based on the timing determination procedure information.

2 Claims, 12 Drawing Sheets

(56) References Cited

U.S. PATENT DOCUMENTS

| | | | |
|---|---|---|---|
| 8,315,448 B2* | 11/2012 | Takei | 382/128 |
| 8,480,571 B2* | 7/2013 | Yamazaki | 600/178 |
| 8,531,512 B2* | 9/2013 | Gono et al. | 348/68 |
| 2007/0211839 A1* | 9/2007 | Suda | 375/354 |
| 2008/0129527 A1* | 6/2008 | Ohyama et al. | 340/679 |
| 2008/0309787 A1 | 12/2008 | Notsu et al. | |
| 2009/0018789 A1 | 1/2009 | Weng et al. | |
| 2009/0030306 A1* | 1/2009 | Miyoshi et al. | 600/424 |
| 2009/0043162 A1* | 2/2009 | Takahashi | 600/118 |
| 2009/0256934 A1 | 10/2009 | Usami et al. | |

FOREIGN PATENT DOCUMENTS

| | | |
|---|---|---|
| JP | 08-079634 | 3/1996 |
| JP | 2001-340290 | 12/2001 |
| JP | 2002-027335 | 1/2002 |
| JP | 2002-077740 | 3/2002 |
| JP | 2003-018477 | 1/2003 |
| JP | 2005-151081 A | 6/2005 |
| JP | 2006-173738 | 6/2006 |
| JP | 2008-311985 | 12/2008 |
| JP | 2009-021977 | 1/2009 |
| JP | 2010-46220 A | 3/2010 |

* cited by examiner

|     | SHD |    |    |    |    |    |    |    |    |     |     |     |
|-----|-----|----|----|----|----|----|----|----|----|-----|-----|-----|
|     | t1  | t2 | t3 | t4 | t5 | t6 | t7 | t8 | t9 | t10 | t11 | t12 |
| t1  | O   |    |    |    |    |    |    |    |    |     |     |     |
| t2  |     |    |    |    |    |    |    |    |    |     |     |     |
| t3  |     |    | O  |    |    |    |    |    |    |     |     |     |
| t4  |     |    |    |    |    |    |    |    |    |     |     |     |
| t5  |     |    |    |    | O  |    |    |    |    |     |     |     |
| t6  |     |    |    |    |    |    |    |    |    |     |     |     |
| t7  |     |    |    |    |    |    | O  |    |    |     |     |     |
| t8  |     |    |    |    |    |    |    |    |    |     |     |     |
| t9  |     |    |    |    |    |    |    |    | O  |     |     |     |
| t10 |     |    |    |    |    |    |    |    |    |     |     |     |
| t11 |     |    |    |    |    |    |    |    |    |     | O   |     |
| t12 |     |    |    |    |    |    |    |    |    |     |     |     |

SHP (row label)

|     | SHD |    |    |    |    |    |    |    |    |     |
|-----|----|----|----|----|----|----|----|----|----|-----|
|     | t1 | t2 | t3 | t4 | t5 | t6 | t7 | t8 | t9 | t10 |
| t1  |    |    |    |    | O  |    |    |    |    |     |
| t2  |    |    |    |    | O  |    |    |    |    |     |
| t3  |    |    |    |    | O  |    |    |    |    |     |
| t4  |    |    |    |    | O  |    |    |    |    |     |
| t5  |    |    |    |    | O  |    |    |    |    |     |
| t6  |    |    |    |    | O  |    |    |    |    |     |
| t7  |    |    |    |    | O  |    |    |    |    |     |
| t8  |    |    |    |    | O  |    |    |    |    |     |
| t9  |    |    |    |    | O  |    |    |    |    |     |
| t10 |    |    |    |    | O  |    |    |    |    |     |

(SHP on left axis)

|     | SHD |    |    |    |    |    |    |    |    |     |
|-----|----|----|----|----|----|----|----|----|----|-----|
|     | t1 | t2 | t3 | t4 | t5 | t6 | t7 | t8 | t9 | t10 |
| t1  |    |    |    |    |    |    |    |    |    |     |
| t2  |    |    |    |    |    |    |    |    |    |     |
| t3  |    |    |    |    |    |    |    |    |    |     |
| t4  | ○  | ○  | ○  | ○  | ○  | ○  | ○  | ○  | ○  | ○   |
| t5  |    |    |    |    |    |    |    |    |    |     |
| t6  |    |    |    |    |    |    |    |    |    |     |
| t7  |    |    |    |    |    |    |    |    |    |     |
| t8  |    |    |    |    |    |    |    |    |    |     |
| t9  |    |    |    |    |    |    |    |    |    |     |
| t10 |    |    |    |    |    |    |    |    |    |     |

SHP (row label)

FIG.20

ENDOSCOPE AND ENDOSCOPE SYSTEM

CROSS REFERENCE TO RELATED APPLICATION

This application is a continuation application of PCT/JP2011/073401 filed on Oct. 12, 2011 and claims benefit of Japanese Application No. 2010-231763 filed in Japan on Oct. 14, 2010, the entire contents of which are incorporated herein by this reference.

BACKGROUND OF THE INVENTION

1. Field of the Invention

The present invention relates to an endoscope and an endoscope system and specifically relates to an endoscope and an endoscope system that perform processing for adjusting sampling timings in correlated double sampling.

2. Description of the Related Art

Conventionally, endoscopes have widely been used in medical and industrial fields. An endoscope system includes an endoscope that includes an elongated insertion portion, and a body portion, and picks up an image of an object by means of an image pickup device provided in a distal end portion of the insertion portion, and processes the image pickup signal in an image processing section of the body portion, and displays an image of the object on a monitor. The image pickup device includes, for example, a CCD, and is driven by a drive signal to output an image pickup signal.

In the endoscope system, in order to remove noise in an analog image pickup signal from the image pickup device, correlated double sampling is used. Correlated double sampling processing is processing for sampling an output signal from the CCD via a feedthrough sampling pulse and a clamp pulse and taking difference between the two signals obtained by the sampling to remove, e.g., reset noise. A correlated double sampling circuit (hereinafter referred to as CDS circuit) is provided in the body portion to which the endoscope is connected or the endoscope itself.

Also, since the lengths of the insertion portions of endoscopes are different depending on the types of endoscopes, the time consumed for an image pickup signal received in response to a drive signal from a drive circuit to reach a CDS circuit is also different. Thus, it is necessary to adjust timings for sampling the received image pickup signal.

For example, at the time of manufacture, the cumbersome work of connecting a measuring device that measures a signal waveform to a signal processing circuit in the body portion, and an adjuster for the circuit manually making, i.e., adjustment of a delay amount in a delay circuit is required for sampling timing adjustment.

Therefore, methods in which a reference signal having predetermined amplitude is generated from an output signal from a CCD and phase adjustment is automatically made based on the reference signal such as disclosed in Japanese Patent Application Laid-Open Publication No. 2001-340290 or 2002-27335 have been proposed.

Also, there is a method in which a signal for sampling is automatically generated from a clock signal superimposed in a blanking period of an output signal from a CCD, using a PLL circuit.

SUMMARY OF THE INVENTION

An endoscope according to an aspect of the present invention includes: an image pickup device drive section that outputs a drive signal for driving an image pickup device provided in an insertion portion of the endoscope; a correlated double sampling section that outputs a post-sampling image pickup signal obtained by sampling an image pickup signal outputted from the image pickup device driven by the drive signal, via a feedthrough sampling pulse and a clamp pulse; a control section that controls a sampling timing of each of the feedthrough sampling pulse and the clamp pulse used in the correlated double sampling section, and evaluates the post-sampling image pickup signal outputted from the correlated double sampling section; and a rewritable storage section that stores timing information on respective timings controlled by the control section, and timing determination procedure information determined by an evaluation range of the post-sampling image pickup signal based on a type of the endoscope, in which the control section, upon receipt of an adjustment instruction for adjustment of the respective timings of the feedthrough sampling pulse and the clamp pulse, rewrites the timing information in the storage section according to a result of evaluation of a plurality of post-sampling image pickup signals obtained by shifting the respective timings based on the timing determination procedure information.

An endoscope system according to an aspect of the present invention includes an endoscope and a body portion to which the endoscope is connected, the endoscope system having an observation mode for observing an object and an adjustment mode for adjusting the endoscope. The body portion includes an adjustment instruction section that provides an instruction to select the adjustment mode. The endoscope includes: an image pickup device drive section that outputs a drive signal for driving an image pickup device provided in an insertion portion of the endoscope; a correlated double sampling section that outputs a post-sampling image pickup signal obtained by sampling an image pickup signal outputted from the image pickup device driven by the drive signal, via a feedthrough sampling pulse and a clamp pulse; a control section that controls a sampling timing of each of the feedthrough sampling pulse and the clamp pulse used in the correlated double sampling section, and evaluates the post-sampling image pickup signal outputted from the correlated double sampling section; and a rewritable storage section that stores timing information on respective timings controlled by the control section, and timing determination procedure information determined by an evaluation range of the post-sampling image pickup signal based on a type of the endoscope. The control section of the endoscope, upon receipt of an instruction to select the adjustment mode from the body portion, rewrites the timing information in the storage section according to a result of evaluation of a plurality of post-sampling image pickup signals obtained by shifting the respective timings of the feedthrough sampling pulse and the clamp pulse based on the timing determination procedure information.

BRIEF DESCRIPTION OF THE DRAWINGS

FIG. 20 is a diagram for describing a range in which where optimum timing positions of a feedthrough sampling pulse SHP and a clamp pulse SHD are determined as timings t4 and t5, respectively, the timing positions are shifted because of temperature change, according to an embodiment of the present invention.

DETAILED DESCRIPTION OF THE PREFERRED EMBODIMENT

An embodiment of the present invention will be described below with reference to the drawings.
(Configuration of Endoscope System)

Figure 1:
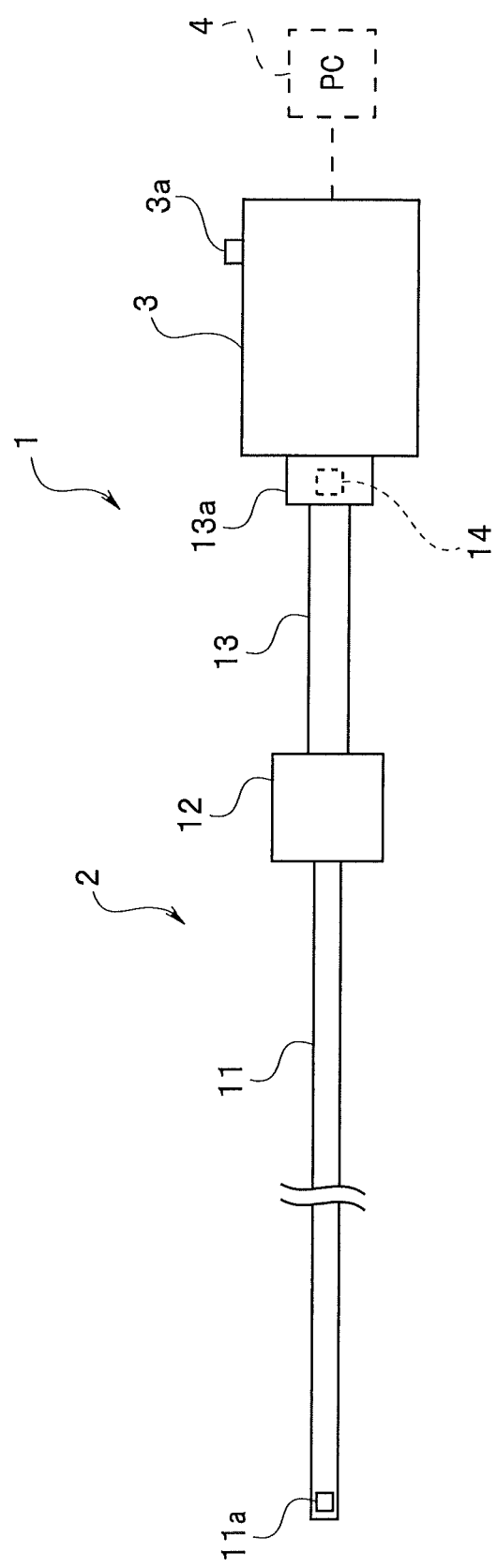
FIG. 1 is a configuration diagram illustrating a configuration of an endoscope system according to an embodiment of the present invention.

First, a configuration of an endoscope system according to the present embodiment will be described with reference to FIG. 1. FIG. 1 is a configuration diagram illustrating a configuration of an endoscope system according to the present embodiment.

As illustrated in FIG. 1, an endoscope system 1 includes an endoscope 2 and a body portion 3. Furthermore, a personal computer (hereinafter referred to as PC) 4 is connectable to the body portion 3.

The endoscope system 1 is an endoscope system having an observation mode for observing an object and an adjustment mode for adjusting the endoscope.

The endoscope 2 has flexibility, and includes an insertion portion 11 that can be inserted into an object, an operation section 12 to which a proximal end portion of the insertion portion 11 is connected, a cable 13 connected to the operation section 12, and a connector 13a provided at an end portion on the distal end side of the cable 13. A CCD 11a, which is an image pickup device, is provided at a distal end portion of the insertion portion 11. The operation section 12 includes various types of operation members (not illustrated) such as knobs and/or buttons for, e.g., bending operation and shooting operation. The cable 13, which includes various types of signal wires for transmission/reception of signals to/from the endoscope 2, is connected to the body portion 3 via the connector 13a.

The cable 13 includes a signal wire for a drive signal for driving the CCD 11a and a signal wire for an image pickup signal from the CCD 11a.

The body portion 3 is provided with a connector (not illustrated) for connection with the connector 13a of the endoscope 2. The body portion 3 includes a video signal processing section that receives an image pickup signal, which is a video signal from the endoscope 2, and subjects the video signal to image processing, and outputs the video signal to a non-illustrated monitor.

The body portion 3 is provided with an operation panel including, e.g., buttons for various types of operations, and a user can conduct an examination using the endoscope 2 by operating the operation panel, and also set the endoscope system 1 into the adjustment mode and provide an adjustment instruction for adjusting timings of image pickup signal sampling, which will be described later, in a CDS circuit. As illustrated in FIG. 1, as one of the buttons in the operation panel, an adjustment instruction button 3a for providing an instruction for sampling timing adjustment is provided at the body portion 3. Accordingly, the adjustment instruction button 3a is an adjustment instruction section for providing an instruction to select the adjustment mode.

Note that although the description below is provided in terms of a case where the later-described sampling timing adjustment processing is performed as a result of the adjustment instruction button 3a being depressed, sampling timing adjustment processing may be performed by a sampling timing adjustment instruction provided via the PC 4 connected to the body portion 3.

The CCD drive adjustment section 14 is provided inside the connector 13a. The CCD drive adjustment section 14 generates a drive signal DR to drive the CCD 11a, receives an image pickup signal from the CCD 11a and outputs the image pickup signal to the body portion 3, and also performs processing for adjusting timings for a feedthrough sampling pulse SHP and a clamp pulse SHD for correlated double sampling of the image pickup signal.

Note that although the CCD drive adjustment section 14 is provided inside the connector 13a in FIG. 1, the CCD drive adjustment section 14 may be provided inside the operation section 12 or the body portion 3.

The endoscope system 1 is installed in, for example, an examination room of a hospital, and is operated by a surgeon to use the endoscope system 1 for an endoscopic examination of the inside of a body cavity of an object. Each of endoscopes 2 used in such endoscopic examinations differs in, e.g., the length of the insertion portion 11, depending on the purpose of the examination, and also, e.g., the number of pixels in the mounted image pickup device differs depending on the type of the endoscope.

(Configuration of CCD Drive Adjustment Section)

Figure 2:
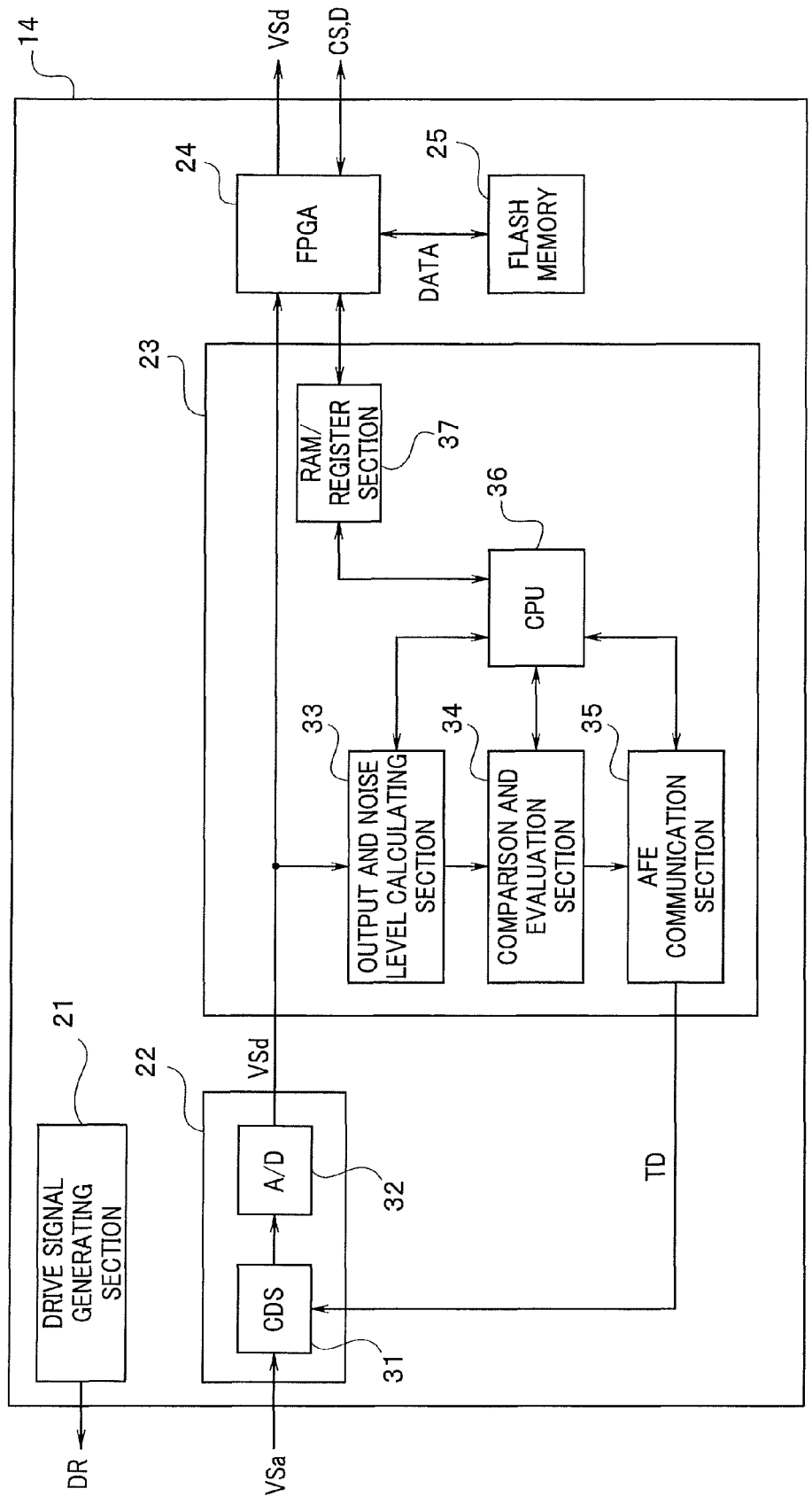
FIG. 2 is a block diagram illustrating a configuration of a CCD drive adjustment section according to an embodiment of the present invention.

FIG. 2 is a block diagram illustrating a configuration of the CCD drive adjustment section 14.

The CCD drive adjustment section 14 includes a drive signal generating section 21 that generates and outputs various types of drive signals DS to the CCD 11a, an analog front-end section (hereinafter referred to as AFE section) 22 to which an image pickup signal VSa, which is an analog signal, from the CCD 11a is inputted, a digital signal processor (hereinafter referred to as DSP) 23, a field programmable gate array (hereinafter referred to as the FPGA) 24 and a flash memory 25, which is a rewritable nonvolatile memory.

The drive signal generating section 21, which is an image pickup device drive section, is a drive circuit that generates various types of drive signals DS, for example, a horizontal drive pulse signal HD, a vertical drive pulse signal VD and a clock signal CLK and outputs these signals to the CCD 11a.

The AFE section 22 includes a CDS circuit 31 and an analog/digital conversion circuit (hereinafter referred to as the A/D conversion circuit) 32. The AFE section 22 subjects an inputted image pickup signal VSa, which is an output signal from the CCD 11a, to correlated double sampling in the CDS circuit 31, converts the image pickup signal VSa into a digital signal in the A/D conversion circuit 32 and outputs an image pickup signal VSd, which is a digital signal. The image pickup signal VSd from the AFE section 22 is supplied to the FPGA 24 via the DSP 23. In other words, the CDS circuit 31 provides a correlated double sampling section that outputs a post-sampling image pickup signal obtained by sampling a pickup signal outputted from the CCD 11a driven by a drive signal DS, via a feedthrough sampling pulse SHP and a clamp pulse SHD.

The DSP 23 includes an output and noise level calculating section 33 that calculates a signal level of an output signal (hereinafter referred to as output level) and a signal level of a noise signal contained in the output signal (hereinafter referred to as noise level), a comparison and evaluation section 34, an analog front-end communication section (hereinafter referred to as AFE communication section) 35, a central processing unit (hereinafter referred to as CPU) 36 and a RAM/register section 37 including a RAM and a register group.

The output and noise level calculating section 33 is a circuit that monitors an image pickup signal VSd outputted from the AFE section 22 and calculates an output level and a noise level of the image pickup signal VSd. The noise level is calculated by comparing an average value of output levels and the respective output levels to figure out the number of pixels or a proportion of pixels whose difference from the average value exceeds a predetermined value.

Note that the noise level may be calculated by any of other arithmetic operations, e.g., calculating, e.g., dispersion or a standard deviation of the output levels or performing FFT processing to figure out intensity distribution of frequencies other than a particular frequency.

The comparison and evaluation section 34 is a circuit that determines timings for sampling an output level and a noise level of an image pickup signal VSd outputted from the output and noise level calculating section 33 based on predetermined timing determination procedure information. While the timing determination procedure information, which is information specific to, that is, a reference to the endoscope 2, is stored in the flash memory 25 in advance, the content of processing in the comparison and evaluation section 34 is common to all of endoscopes.

The AFE communication section 35 is a circuit that transmits timing data TD indicating sampling timings for a feedthrough sampling pulse SHP and a clamp pulse SHD to the AFE section 22 by means of serial communications. The timing data TD is sampling timing information for a feedthrough sampling pulse SHP and a clamp pulse SHD.

The AFE communication section 35 outputs timing data TD read by the CPU 36 from the flash memory 25 to the AFE section 22 during normal use of the endoscope 2, and outputs timing data TD that varies according to an instruction from the CPU 36 to the AFE section 22 during sampling timing adjustment processing.

In the CDS circuit 31, an image pickup signal is sampled at respective sampling timings of a feedthrough sampling pulse SHP and a clamp pulse SHD, which are designated by the timing data TD from the AFE communication section 35 in the DSP 23.

The CPU 36 is a control section that is connected to the output and noise level calculating section 33, the comparison and evaluation section 34, the AFE communication section 35 and the RAM/register section 37 and controls overall operation of the DSP 23. The CPU 36 incorporates a software program or a hardware circuit therein, the software program or the hardware circuit performing processing for adjusting timings of sampling an image pickup signal, which will be described later.

The comparison and evaluation section 34, the AFE communication section 35 and the CPU 36, which have been described above, provide a control section that controls respective sampling timings for a feedthrough sampling pulse SHP and a clamp pulse SHD used in the CDS circuit 31 and evaluates a post-sampling image pickup signal outputted from the CDS circuit 31.

The RAM/register section 37 is a storage section that provides temporary storage for data communication between the CPU 36 and the FPGA 24. Note that in the present embodiment, the storage section, which is the RAM/register section 37, includes both a RAM and a register group, but may include any one of the RAM and the register group.

The FPGA 24 is a circuit that performs communication between the endoscope 2 and the body portion 3, and thus, is a circuit for transmission/reception of control signals CS and data D between the endoscope 2 and the body portion 3, the circuit letting an image pickup signal VSd through and outputting the image pickup signal VSd to the body portion 3. The image pickup signal VSd is transmitted to the body portion 3 by means of a serial transmission method, for example, an LVDS method.

The control signals CS and the data D are received/transmitted to/from the body portion 3 and the endoscope 2 by means of the serial transmission method. The control signals CS and the data D communicated between the endoscope 2 and the body portion 3 are control signals (including an adjustment command) and data for normal use and adjustment of the endoscope 2. Accordingly, the FPGA 24 provides a communication section that receives an adjustment instruction as serial data.

Furthermore, the FPGA 24 has a function that performs reading/writing of data between the CPU 36 and the flash memory 25.

The data communication between the CPU 36 and the FPGA 24 is performed by writing data to the RAM/register section 37. The FPGA 24 writes data to a predetermined storage area of the RAM/register section 37, whereby the CPU 36 acquires data or a command. The CPU 36, upon receipt of a command, performs processing based on the command, for example, the later-described sampling timing adjustment processing. Also, the CPU 36 writes data to a predetermined area of the RAM/register section 37, whereby the data can be written to the flash memory 25 via the FPGA 24. The FPGA 24 is used, for example, when timing information determined in sampling timing adjustment processing is written to the flash memory 25 or stored timing information is read from the flash memory 25.

In the flash memory 25, which is a rewritable storage section, timing information for each of a feedthrough sampling pulse SHP and a clamp pulse SHD in the CDS circuit 31 and timing determination procedure information are stored.

The timing determination procedure information is data containing information such as parameters for adjustment in respective search processings, which will be described later, determination criteria and various type of environment setting information for adjustment, and is stored in the flash memory 25 in advance.

The timing information includes data on respective sampling timings (positions) of a feedthrough sampling pulse SHP and a clamp pulse SHD, which are determined by the later-described sampling timing adjustment processing.

The adjustment parameters in the timing determination procedure information differ depending on the endoscope, and as described later, contains data on a range of output level (and noise level) detection during a search and data on a range in which a respective sampling timing is shifted and sampling positions in each of a feedthrough waveform part and an output waveform part of an image pickup signal corresponding to one pixel in each of a rough search and a fine search.

The determination criteria in the timing determination procedure information contain reference data for determining whether a timing (position) of sampling is determined by evaluating output levels only or comparing and evaluating both output levels and noise levels.

The environment setting information in the timing determination procedure information includes, e.g., gains of the circuits and set values for a light source apparatus in each of the later-described respective searches when the CPU 36 shifts the respective timings to obtain a plurality of post-sampling image pickup signals.

Accordingly, the flash memory 25 provides a rewritable storage section that stores timing information on the respective timings controlled by the CPU 36 and the timing determination procedure information.

As described above, the control signals CS from the body portion 3 are supplied to the CPU 36 via the FPGA 24. Furthermore, the CPU 36 performs reading of data from the flash memory 25 and writing of data to the flash memory 25 via the FPGA 24. At this time, between the FPGA 24 and the CPU 36, data is transmitted/received via the RAM/register section 37. The control signals CS from the body portion 3 also contain a command for a sampling timing adjustment instruction (hereinafter referred to as adjustment command), which will be described later.

(Sampling Timing Adjustment Processing)

Next, processing for adjusting respective sampling timings of a feedthrough sampling pulse SHP and a clamp pulse SHD will be described. Sampling timing adjustment processing is performed at the time of manufacture or repair of the endoscope 2.

An adjustment instruction for providing an instruction to perform sampling timing adjustment processing is provided by a user operating the adjustment instruction button 3a in the body portion 3. In response to the operation of the adjustment instruction button 3a, a control signal CS, which is an adjustment command, is supplied from the body portion 3 to the CPU 36 via the FPGA 24.

Figure 3:
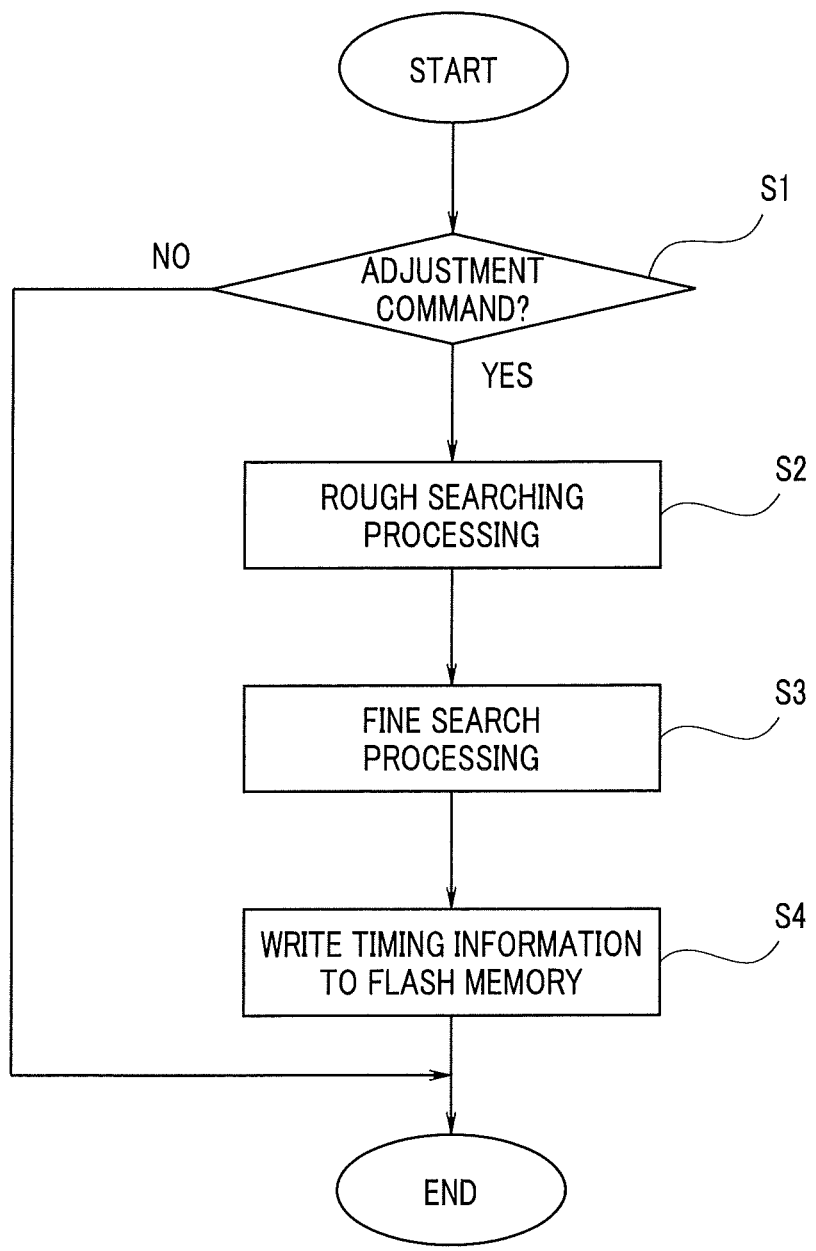
FIG. 3 is a flowchart illustrating an example of the flow of sampling timing adjustment processing according to an embodiment of the present invention, the sampling timing adjustment processing being performed when an adjustment command is received.

The CPU 36, upon receipt of the adjustment command, performs the processing illustrated in FIG. 3. FIG. 3 is a flowchart illustrating an example of the flow of sampling timing adjustment processing performed when an adjustment command is received. First, the CPU 36 determines whether or not the received control signal CS is an adjustment command (S1).

If the control signal CS is not an adjustment command (S1: NO), the processing is terminated. If the control signal CS is an adjustment command (S1: YES), the CPU 36 performs rough search processing for performing a rough search for a sampling timing (S2).

Figure 4:
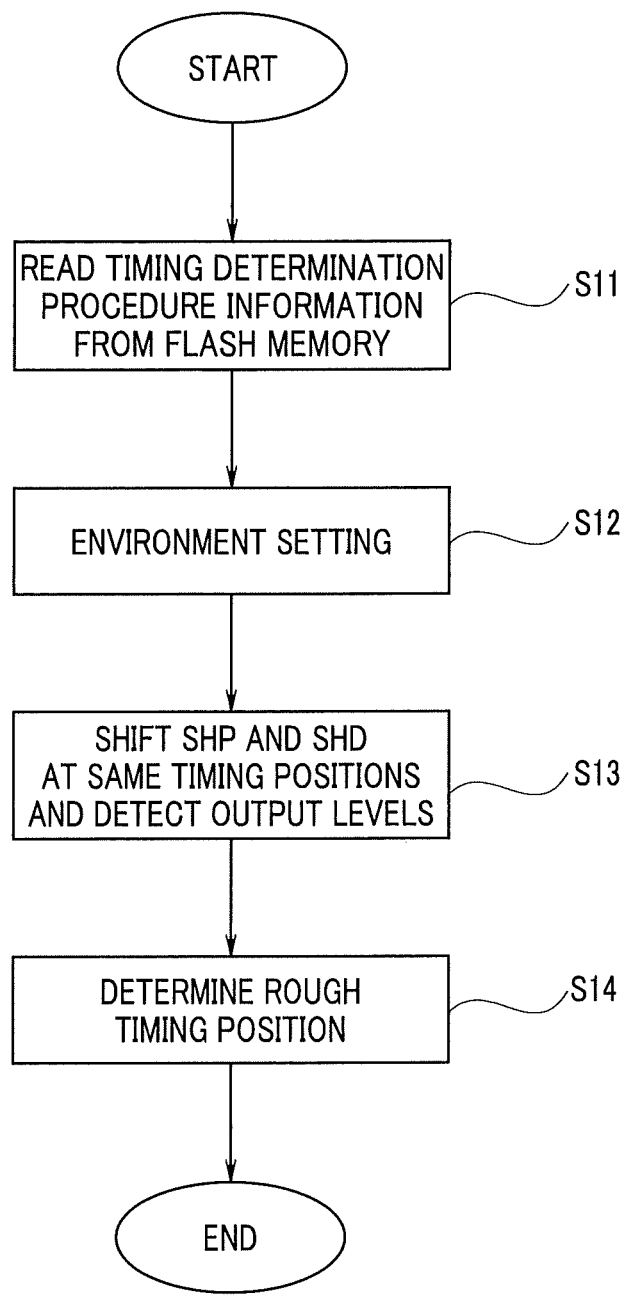
FIG. 4 is a flowchart illustrating an example of the flow of rough search processing according to an embodiment of the present invention.

FIG. 4 is a flowchart illustrating an example of the flow of rough search processing. First, the CPU 36 reads timing determination procedure information necessary for performing rough search processing, from the flash memory 25 (S11).

The timing determination procedure information contains information on a range of output level calculation in an effective pixel range and information on a reference position and sampling positions for timing shifting during a search as adjustment parameters, and information on, e.g., gain values of circuits and set values for a light source used in rough search processing as environment setting information, and further contains information for sampling timing determination in a rough search as a determination criterion.

The CPU 36 makes various types of settings for, e.g., various types of circuits and the light source apparatus based on the read environment setting information (S12).

The CPU 36 shifts a timing position of a feedthrough sampling pulse SHP and a timing position of a clamp pulse SHD at the same timing position, as described later, using the read timing determination procedure information, and detects output levels at each of the shifted positions (S13). The output level detection processing in S13 is performed in the output and noise level calculating section 33 in FIG. 2.

The CPU 36 determines a timing at which the output level has a largest value from among a plurality of detected output levels as a timing position in the rough search processing (S14). The processing in S14 is performed in the comparison and evaluation section 34 under the CPU 36.

By the rough search processing, rough timings (positions) of the feedthrough sampling pulse SHP and the clamp pulse SHD are searched for and determined.

Figure 5:
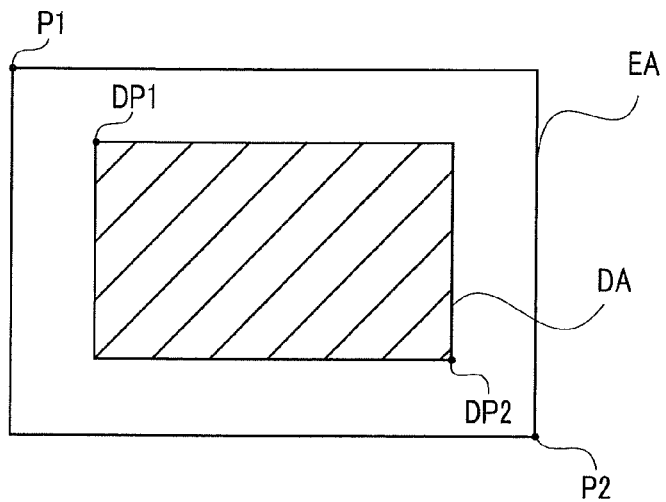
FIG. 5 is a diagram illustrating an output level (and noise level) detection range in an effective pixel range according to an embodiment of the present invention.

FIG. 5 is a diagram for describing a range of output level (and noise level) detection in an effective pixel range. In FIG. 5, an effective pixel range EA is defined by a reference position P1(0, 0) and a final position P2(N, M) (N and M are integers), and a calculation range DA is defined by positions DP1 (a1, b1) (a1 and b1 are integers) and DP2 (a2, b2) (a2 and b2 are integers) in the effective pixel range EA.

A case where the CCD 11a has a large number of pixels and a case where the CCD 11a has a small number of pixels are different from each other in terms of a range DA suitable for calculation of output levels (and noise levels (when noise levels are detected in the later-described fine search processing)) in the effective pixel range EA. This is because there are endoscopes that do not use a part of the effective pixel range EA and thus are optically set so that no light enters such part and endoscopes whose way of light incidence is different from that of direct-viewing endoscopes, such as perspectiveviewing or side-viewing endoscopes, and thus, it is necessary to use only an range on which light is incident for the respective endoscope. Another reason is that it is desirable to use as many pixels as possible because as the number of pixels subject to calculation is larger, the effect of variations in characteristics among the pixels is smaller.

The number of pixels in an image pickup device used in an endoscope is determined according to the type of the endoscope, and the optical design is also determined, and thus, a detection range DA subject to calculation is also determined depending on the type of the endoscope.

Accordingly, information on the detection range DA is written and stored in advance in the flash memory 25 as a piece of adjustment parameter data, and at the time of a rough search (and at the time of a later-described fine search), such piece of information is read and used by the CPU 36.

Next, processing for the CPU 36 to determine a procedure for determining timings of a feedthrough sampling pulse SHP and a clamp pulse SHD will be described.

Figure 6:
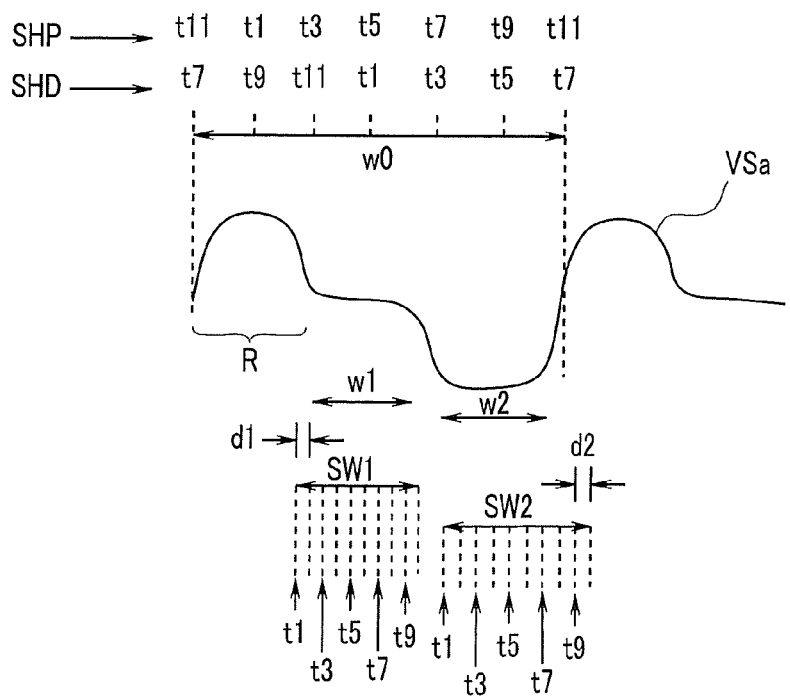
FIG. 6 is a diagram for describing a method for shifting positions of timings of a feedthrough sampling pulse SHP and a clamp pulse SHD according to an embodiment of the present invention.

FIG. 6 is a diagram for describing a method for shifting timing positions of a feedthrough sampling pulse SHP and a clamp pulse SHD. As illustrated in FIG. 6, an image pickup signal part w0 corresponding to one pixel in an image pickup signal VSa outputted from the CCD 11a includes a feedthrough waveform part w1 and an output waveform part w2. It is necessary that the image pickup signal VSa be sampled at proper sampling timings in each of the feedthrough waveform part w1 and the output waveform part w2.

Since the length of the image pickup signal part w0 corresponding to one pixel in the image pickup signal VSa is determined in advance depending on the type of the CCD 11a, for example, a period of one pixel, information on a search range and sampling positions in rough search processing are stored in advance in the flash memory 25 as adjustment parameter data for the relevant endoscope 2 according to, e.g., the period of one pixel determined in advance.

In the rough search processing, the CPU 36 performs search processing using these pieces of information for rough search processing.

Since respective positions (or timings) of the feedthrough waveform part w1 and the output waveform part w2 in the image pickup signal VSa in the received image pickup signal VSa are unknown, the search range for a rough search is the entire range of the image pickup signal part w0 corresponding to one pixel in the image pickup signal VSa, and sampling positions for a rough search are determined by dividing the image pickup signal part w0 by a predetermined number.

It is possible that the search range for a rough search is not the entire range of the image pickup signal part w0 but is a part of the image pickup signal part w0.

Accordingly, positions of timings for sampling in the rough search processing are determined in advance as positions, that is, timings for sampling the image pickup signal VSa in the image pickup signal part w0, which is a search range, the positions being determined by a predetermined period based on, e.g., the number of pixels, and at each of the predetermined timing positions, an output level is detected.

For example, as illustrated in FIG. 6, where the image pickup signal part w0 is divided by a predetermined period d into twelve, in rough search processing, sampling is performed at six timings, i.e., first, third, fifth, seventh, ninth and eleventh timings (that is, sampling positions) t1, t3, t5, t7, t9 and t11 from among the twelve timings in the image pickup signal part w0. However, as illustrated in FIG. 6, the positions of the feedthrough sampling pulse SHP and the positions of the clamp pulse SHD are numbered with shifted from each other by a predetermined number, and the respective samplings are performed in the same order of sampling numbers.

An error in a reset part R is cancelled by taking difference in signal waveform between the reset part R and an OB (optical black) part.

The feedthrough sampling pulse SHP and the clamp pulse SHD are outputted at six same timings t1, t3, t5, t7, t9 and t11.

Figures 7, 8:
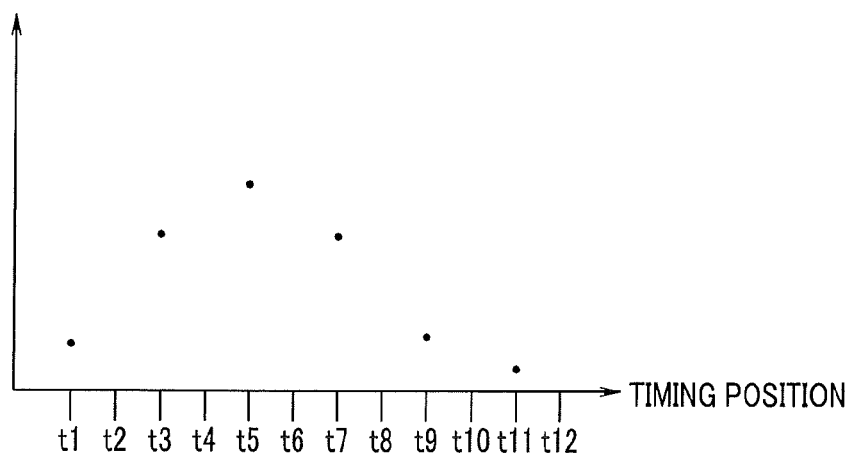
FIG. 7 is a diagram for describing timings for sampling in rough search processing according to an embodiment of the present invention.
FIG. 8 is a graph illustrating an example of output level values obtained in rough search processing according to an embodiment of the present invention.

FIG. 7 is a diagram for describing timings for sampling in rough search processing. The matrix illustrated in FIG. 7 indicates that the timing positions of the feedthrough sampling pulse SHP and the clamp pulse SHD are both timings t1, t3, t5, t7, t9 and t11.

In the rough search processing, the CPU 36 determines a timing at which a largest output level has been obtained from among output levels of the image pickup signal obtained by shifting the timing positions of the feedthrough sampling pulse SHP and the clamp pulse SHD at the same timings t1, t3, t5, t7, t9 and t11.

FIG. 8 is a graph illustrating an example of output level values obtained in the rough search processing. As illustrated in FIG. 8, the output level at the timing position t5 is the largest value. Accordingly, the CPU 36 and the comparison and evaluation section 34 determine the timing t5, which is a timing at which the largest output level has been obtained as a rough timing position in S14.

Referring back to FIG. 3, after the rough search processing (S3), fine search processing is performed. In the fine search processing, the CPU 36 performs search processing using information for fine search processing in the timing determination procedure information. Although the information for fine search processing contains a search range and sampling positions in the image pickup signal VSa, here, the information for fine search processing contains a search range and sampling positions that are the same as those for a rough search.

Figure 9:
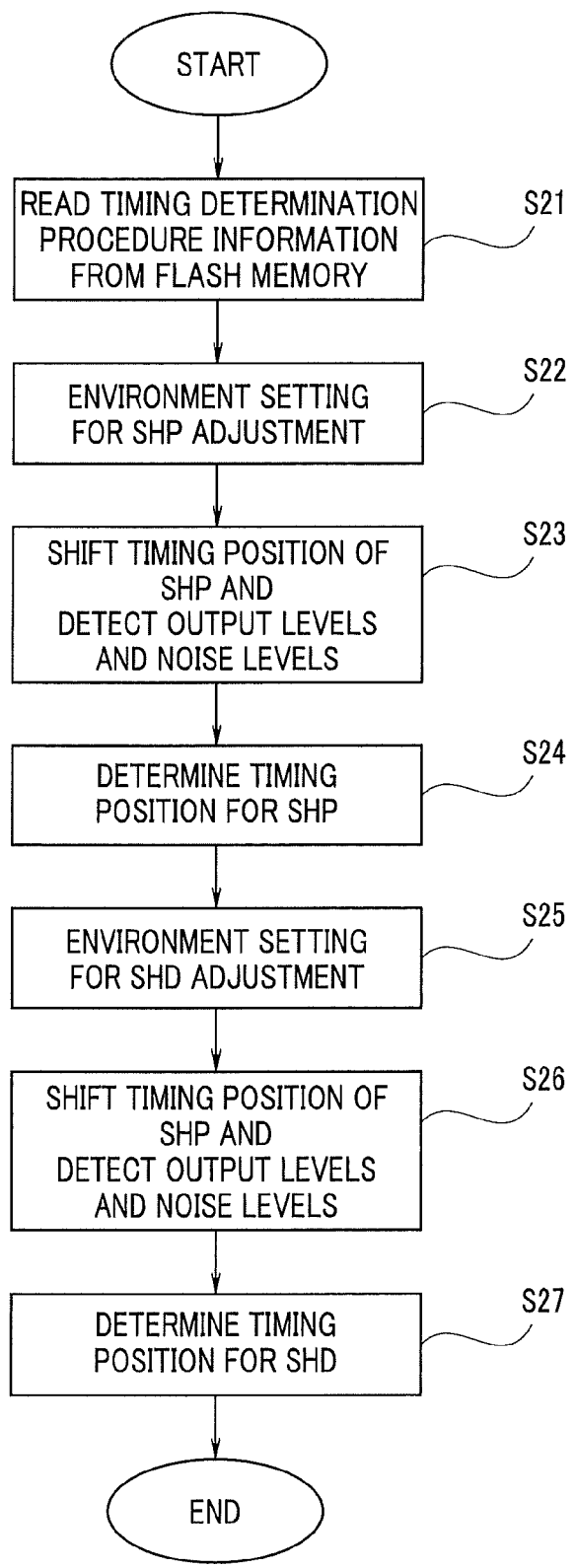
FIG. 9 is a flowchart illustrating an example of the flow of fine search processing according to an embodiment of the present invention.

FIG. 9 is a flowchart illustrating an example of the flow of the fine search processing. First, the CPU 36 reads timing determination procedure information necessary for performing fine search processing, from the flash memory 25 (S21).

The timing determination procedure information contains information on a range of output level and noise level calculation in an effective pixel range and information on a reference position and sampling positions for timing shifting during a search as adjustment parameter data, and information such as gain values of circuits and set values for a light source used in fine search processing as environment setting information, and further contains information for sampling timing determination as a determination criterion.

The CPU 36 makes various types of settings for, e.g., various types of circuits and the light source apparatus based on the read environment setting information in order to make timing position adjustment for the feedthrough sampling pulse SHP (S22).

Next, using the read timing determination procedure information, the CPU 36 fixes the timing position of the clamp pulse SHD, shifts the feedthrough sampling pulse SHP and detects an output level and a noise level at each of the shifted positions (S23). The output level detection processing in S23 (and S26, which will be described later) is performed in the output and noise level calculating section 33 in FIG. 2.

A more specific description will be provided using the above example. Where the timing t5 is determined as a rough timing position in the image pickup signal part w0 by the rough search processing, first, with the timing position of the clamp pulse SHD fixed at the position t5 determined by the rough search processing, as illustrated in FIG. 6, a new search range SW1 with the timing t5 as a benchmark, and the new search range SW1 is divided into, for example, ten, and the feedthrough sampling pulse SHP is shifted from timing position t1 to t10 in the search range SW1, and an output level and a noise level are detected for each of the shifted positions.

The search range SW1 is a search range SW1 that is set in advance and is larger than the feedthrough waveform part w1 so that each optimum timing can be searched for, and the sampling positions are positions in the search range SW1.

Figures 10, 11:
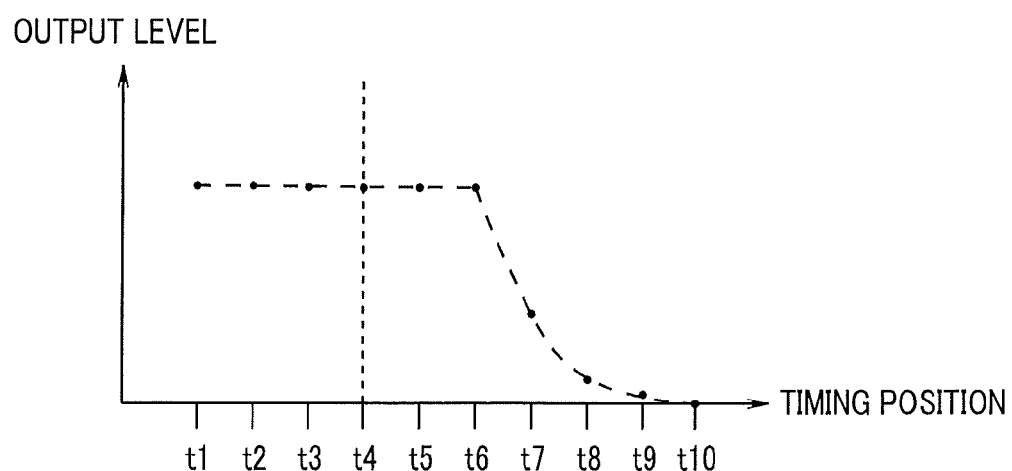
FIG. 10 is a diagram for describing timings for performing sampling while a feedthrough sampling pulse SHP is shifted in the order of timing positions t1 to t10 with a timing position of a clamp pulse SHD fixed at t5, according to an embodiment of the present invention.
FIG. 11 is a graph of respective output levels detected at respective timing positions according to an embodiment of the present invention.

FIG. 10 is a diagram for describing timings for performing sampling when the timing position of the feedthrough sampling pulse SHP is shifted from the timing position t1 to t10 with the timing position of the clamp pulse SHD fixed at, for example, t5. The matrix illustrated in FIG. 10 indicates that sampling is performed at each of all the timings (that is, ten sampling positions) t1, t2, t3, t4, t5, t6, t7, t8, t9 and t10 using the feedthrough sampling pulse SHP with the timing position of the clamp pulse SHD fixed at the timing t5.

FIG. 11 is a graph of respective output levels detected at the respective timing positions. As illustrated in FIG. 11, where the sampling positions of the feedthrough sampling pulse SHP are timings t1 to t6, the output levels are large values that are substantially equal to one another.

The CPU 36 compares and evaluates the detected output levels based on the read determination criterion, and determines the timing t4 as a position for sampling timing for the feedthrough sampling pulse SHP (S24). The processing in S24 is performed in the comparison and evaluation section 34 under the control of the CPU 36.

The determination criterion contains a reference or a rule of where there are output levels that are equal to or exceeding a predetermined value and substantially the same values continue (in the case of FIG. 11, the flat part from the timings t1 to t6 in the graph), selecting a center timing to determine the center timing as an optimum timing position. Accordingly, in the case of FIG. 11, a timing t4 (which may also be t3) is determined as an optimum timing position for the feedthrough sampling pulse SHP.

Next, the CPU 36 makes various types of settings for, e.g., various types of circuits and a light source apparatus based on the read environment setting information in order to make timing position adjustment for the clamp pulse SHD (S25).

Next, using the read timing determination procedure information, the CPU 36 fixes the timing position of the feedthrough sampling pulse SHP, shifts the clamp pulse SHD and calculates, that is, detects an output level and a noise level at each of the shifted positions (S26).

Then, the CPU 36 compares and evaluates the detected output levels or the detected output levels and the detected noise levels based on the determination criterion in the read timing determination procedure information to determine a position for sampling timing for the clamp pulse SHD (S27). The processing in S27 is performed in the comparison and evaluation section 34 under the CPU 36.

A more specific description will be provided using the above example. Since the timing position of the feedthrough sampling pulse SHP has been determined as the timing t4 in S24, as illustrated in FIG. 6, with the timing position of the feedthrough sampling pulse SHP fixed at t4, a new search range SW2 is set with the timing t5 as a benchmark, and the search range SW2 is divided into, for example, ten, and the clamp pulse SHD is shifted from timing positions t1 to t10 in the search range SW2, and an output level and a noise level are detected for each of the shifted positions.

The search range SW2 is a search range SW2 that is set in advance, enables a search for each optimum timing and is wider than the output waveform part w2, and sampling positions are positions in the search range SW2.

Figures 12, 13:
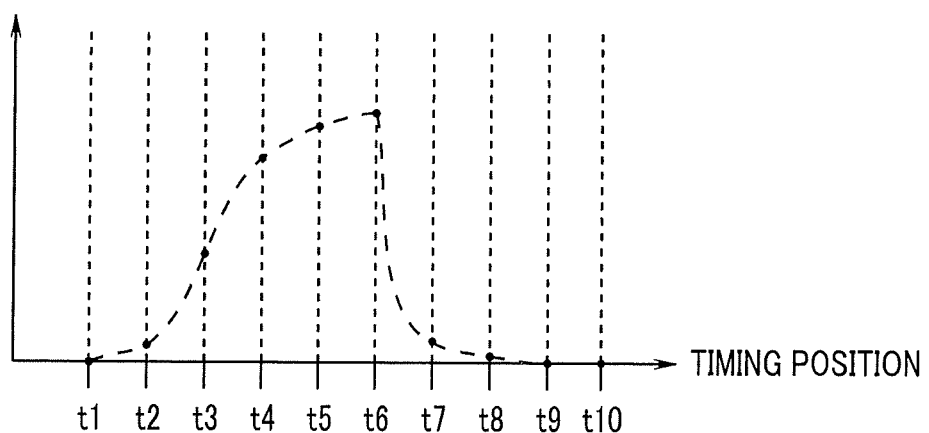
FIG. 12 is a diagram for describing timings for performing sampling while a clamp pulse SHD is shifted from timing position t1 to t10 with a timing position of a feedthrough sampling pulse SHP fixed at t4, according to an embodiment of the present invention.
FIG. 13 is a graph of respective output levels detected at respective timing positions according to an embodiment of the present invention.

FIG. 12 is a diagram for describing timings for sampling when the clamp pulse SHD is shifted from the timing positions t1 to t10 with the timing position of the feedthrough sampling pulse SHP fixed at t4. The matrix illustrated in FIG. 12 indicates that sampling is performed at each of all the timings (that is, ten sampling positions) t1, t2, t3, t4, t5, t6, t7, t8, t9 and t10 using the clamp pulse SHD with the timing position of the feedthrough sampling pulse SHP fixed at the timing t4.

FIG. 13 is a graph of respective output levels detected at the respective timing positions. As illustrated in FIG. 13, from the timings t3 to t6 of the clamp pulse SHD, the output level increases, but at the positions before and after these positions, the output level is low. At the timing t6, the output level exhibits a peak value, and at the timing t5, the output level exhibits a value lower than the peak value.

In the case of FIG. 13, the CPU 36 evaluates the detected output levels based on the read determination criterion, and determines the timing t5 as an optimum timing position for the clamp pulse SHD.

More specifically, the determination criterion contains information on whether an optimum timing position is determined based on the output levels only or an optimum timing position is determined based on the output levels and the noise levels.

For example, if the number of pixels is relatively small and/or if the image pickup signal has a relatively low output frequency, a period of timings with stable output levels lasts long, and thus, an optimum timing position is determined based only on the obtained output levels without referring to the noise levels. On the other hand, if the number of pixels is relatively large and/or if the image pickup signal has a relatively high output frequency, a period of timings with stable output levels lasts short, and thus, an optimum timing position is determined from the obtained output levels, taking the noise levels into account.

The information on the determination criterion, which is determined in advance for the respective endoscopes, is stored in advance in the flash memory 25, and thus, based on the determination criterion, an optimum timing position is determined only from the obtained output levels or an optimum timing position is determined not only from the obtained output levels but also taking the noise levels into account. In the case of FIG. 13, based on the determination criterion, the timing t5 is determined as an optimum timing position, taking the noise levels into account.

Referring back to FIG. 3, the CPU 36 writes the determined optimum timing information (that is, the timing position information) for each of the feedthrough sampling pulse SHP and the clamp pulse SHD to the flash memory 25 as timing information (S4).

As described above, the CPU 36, upon receipt of an instruction for timing adjustment for each of the feedthrough sampling pulse SHP and the clamp pulse SHD, rewrites the timing information in the flash memory 25 according to a result of evaluation of a plurality of post-sampling image pickup signals obtained by shifting the respective timings based on the timing determination procedure information.

As described above, the processing in FIG. 3 is performed at the time of manufacture or at the time of repair, and timing information indicating an optimum timing position for each of the feedthrough sampling pulse SHP and the clamp pulse SHD is stored in the flash memory 25, and at the time of use of the endoscope 2 in the observation mode, when the endoscope system 1 is started, the CPU 36 reads the optimum timing information for each of the feedthrough sampling pulse SHP and the clamp pulse SHD, which is stored in the flash memory 25, and supplies the optimum timing information to the AFE section 22 as timing data TD, enabling the CDS circuit to perform correlated double sampling at optimum timings.

Note that although in FIG. 9, the timing position of the clamp pulse SHD is determined after the timing position of the feedthrough sampling pulse SHP is determined, after the determination of the timing position clamp pulse SHD, processing for determining the timing position of the feedthrough sampling pulse SHP may be performed based on the determined timing position of the clamp pulse SHD.

Here, the timing determination criterion information will further be described taking an example. Here, an example of a case of the clamp pulse SHD will be described.

Figure 14:
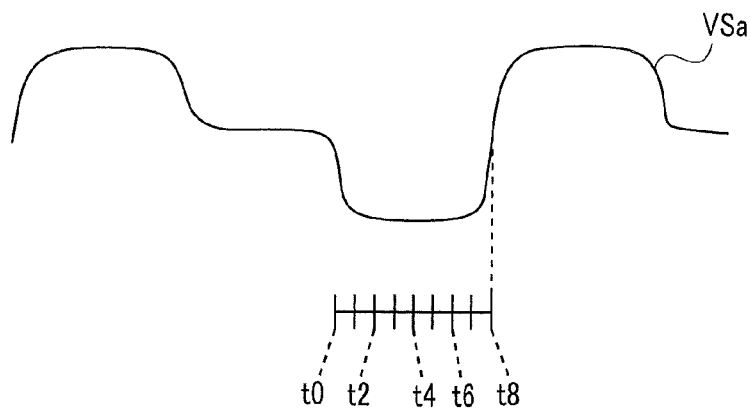
FIG. 14 is a diagram for describing a waveform of an image pickup signal corresponding to one pixel and sampling timings where the image pickup signal is temporally long, according to an embodiment of the present invention.
Figure 15:
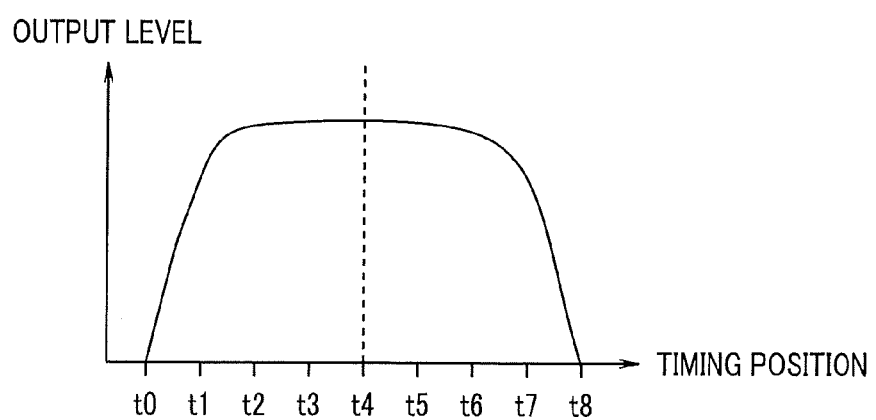
FIG. 15 is a schematic diagram of an output level waveform of the image pickup signal in the case of FIG. 14.
Figure 16:
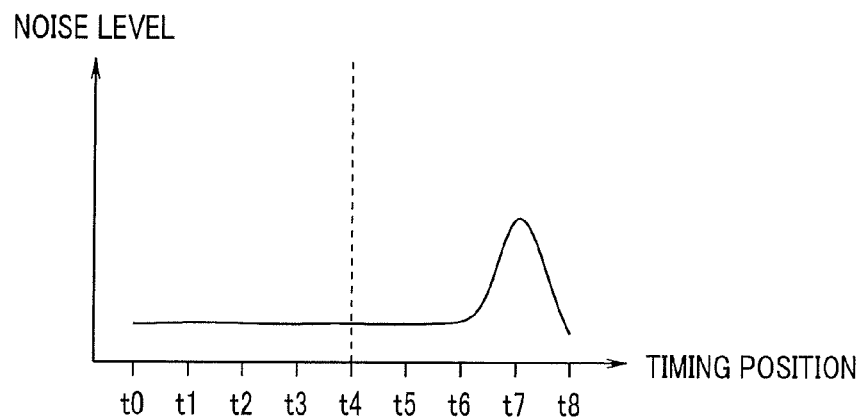
FIG. 16 is a schematic diagram of a noise level waveform of the image pickup signal in the case of FIG. 14.

A waveform period of the image pickup signal VSa is determined by, e.g., the number of pixels in the image pickup device. FIG. 14 is a diagram for describing a waveform of an image pickup signal and sampling timings where a temporal length of the image pickup signal corresponding to one pixel is long (in other words, the image pickup signal has a low frequency). FIG. 15 is a schematic diagram of an output level waveform of the image pickup signal in the case of FIG. 14. FIG. 16 is a schematic diagram of a noise level waveform of the image pickup signal in the case of FIG. 14. Note that FIGS. 14 to 16 indicate an example in which the aforementioned division number is eight.

When an optimum timing for the clamp pulse SHD is determined, as illustrated in FIG. 15, the output level has a large range in which a relatively-large output level is maintained. In the case of FIG. 15, there is a flat range (t2 to t6) in which the output levels are relatively large and substantially equal to one another in the output levels. For the range (t2 to t6), it is desirable to set the timing position to a timing position at which the output level is stable, for example, a timing position in the vicinity of a center of that range (t2 to t6). Furthermore, as illustrated in FIG. 16, the noise level is also stable in that range (t2 to t6).

Accordingly, if an image pickup signal from the endoscope 2 has a low frequency, each optimum timing position for the clamp pulse SHD can be determined based only on the output levels. The same applies to the feedthrough sampling pulse SHP. In the case of an endoscope 2 in which an image pickup signal has a low frequency, the determination criterion stored in the timing determination procedure information stored in the flash memory 25 contains reference data to the effect that data only on output levels is used without using noise levels.

Figure 17:
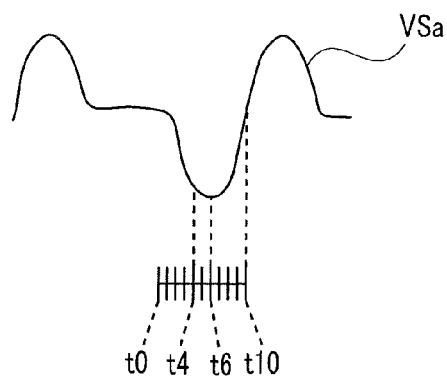
FIG. 17 is a diagram for describing a waveform of an image pickup signal corresponding to one pixel and sampling timings where the image pickup signal is temporally short, according to an embodiment of the present invention.
Figure 18:
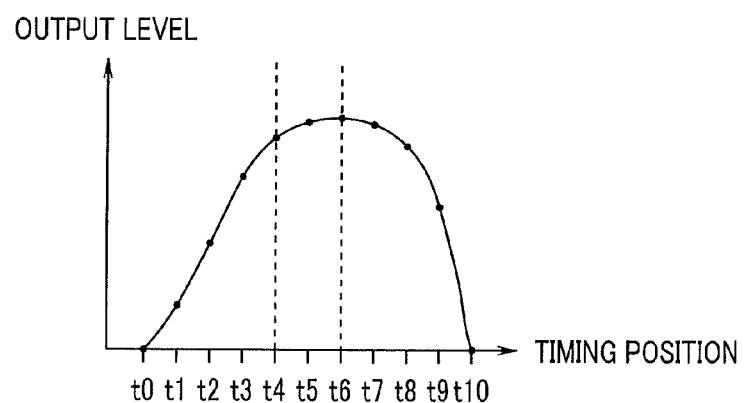
FIG. 18 is a schematic diagram of an output level waveform of the image pickup device in the case of FIG. 17.
Figure 19:
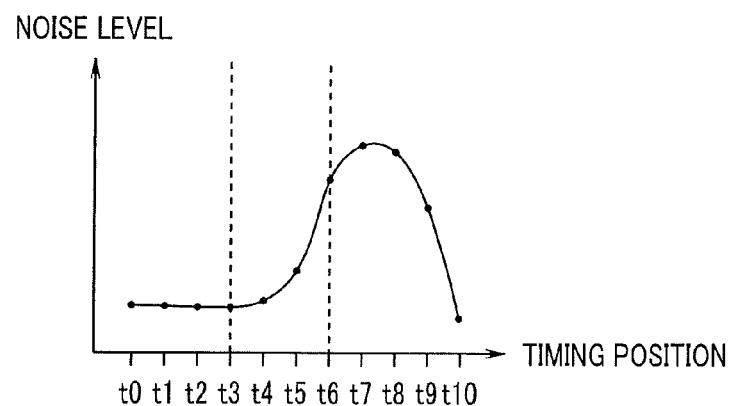
FIG. 19 is a schematic diagram of a noise level waveform of the image pickup device in the case of FIG. 17.

FIG. 17 is a diagram for describing a waveform of an image pickup signal and sampling timings where a temporal length of the image pickup signal corresponding to one pixel is short (in other words, the image pickup signal has a high frequency). FIG. 18 is a schematic diagram of an output level waveform of the image pickup device in the case of FIG. 17. FIG. 19 is a schematic diagram of a noise level waveform of the image pickup device in the case of FIG. 17. Note that FIGS. 17 to 19 indicate an example in which the aforementioned division number is ten.

As illustrated in FIG. 17, when an optimum timing for the clamp pulse SHD is determined, there is no flat range in which the output levels are substantially equal to one another such as illustrated in FIG. 15 in the output levels. Furthermore, as illustrated in FIG. 19, the noise level exhibits a large value in a somewhat large range.

In a case such as shown in FIGS. 17 to 19, an optimum timing position should not be determined based solely on the output levels, but a timing position at which the output level is stable and the noise level is smaller than a predetermined value should be selected. In other words, a condition or a rule for selecting a timing at which the output level has a predetermined threshold value (th1) or more and the noise level has a threshold value (th2) or less is contained in the determination criterion.

Accordingly, where the image pickup signal has a high frequency, respective optimum timing positions for the clamp pulse SHD can be determined not only based on the output levels but also taking the noise levels into account. The same applies to the feedthrough sampling pulse SHP. In the case of an endoscope 2 in which an image pickup signal has a high frequency, the determination criterion in the timing determination procedure information stored in the flash memory 25 contains reference data to the effect that output level data and noise level data are used.

Even though an optimum timing position for each of a feedthrough sampling pulse SHP and a clamp pulse SHD has been determined as described above, the output level and the noise level may change depending on the temperature characteristics. However, the optimum timing position for each of the feedthrough sampling pulse SHP and the clamp pulse SHD, which has been determined in such a manner as described above, is a position that is most stable against temperature change. Even if the timing position is delayed because of an increase in ambient temperature, variation of the timing position is highly likely to remain within a range in which the output level is relatively high and the noise level is relatively low.

Figure 20:
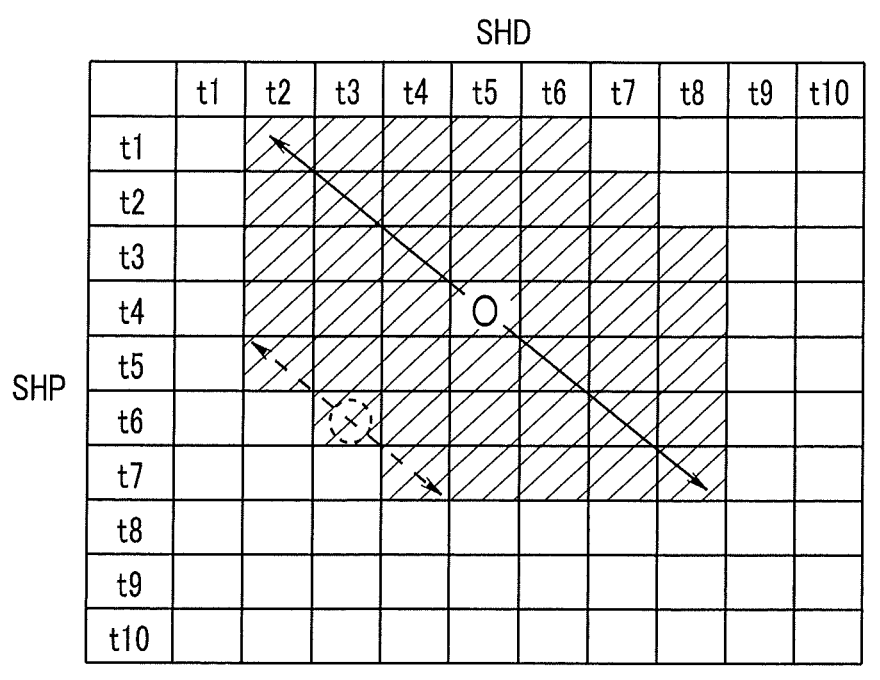

FIG. 20 is a diagram for describing a range in which where, for example, respective optimum timing positions for the feedthrough sampling pulse SHP and the clamp pulse SHD are determined as timings t4 and t5 in the above example, the range in which the timing positions vary because of temperature change.

Even if the timings are advanced or delayed as indicated by the solid arrow relative to the position indicated by the solid circle because of temperature change, the timings are highly likely to remain within a good S/N ratio range (range indicated by shading). However, if the respective timing positions for the feedthrough sampling pulse SHP and the clamp pulse SHD are set in the position, as indicated by the dotted circle, the timings are advanced or delayed as indicated by the dotted arrow because of temperature change, resulting in a decrease in probability that the timings remain in the good S/N ratio range (range indicated by shading).

In recent years, because of miniaturization of circuits accompanying an increase in the number of pixels in image pickup devices, a signal level of an image pickup signal outputted from an image pickup device is small, which may result in impossibility of superimposing a reference signal having a sufficient amplitude on an output signal from a CCD.

Also, in the case of a method using a PLL circuit, since a PLL circuit is a large-scale circuit, a PLL circuit can be mounted in a body portion, but there may be difficulty in mounting a PLL circuit in an endoscope itself.

Furthermore, with an increase in the number of pixels in image pickup devices, the frequency of a drive signal for such an image pickup device also becomes higher, and thus, it is necessary to make adjustment of timings for sampling an image pickup signal not only at the time of manufacture of the endoscope system, but also at the time of repair of the endoscope even when a distal end of a cable is cut and the length of a signal wire extending in the insertion portion is thereby reduced. If the length of the signal wire is changed, no proper image pickup signal can be obtained at sampling timings before the repair, resulting in a decrease in image quality of endoscope images.

Furthermore, there are various types of endoscopes depending on, e.g., the types and/or the pixel counts of the image pickup devices. Accordingly, sampling timing adjustment can be made using various types of parameters for the respective endoscope. However, storing the respective parameters for each of all the endoscopes in an adjustment apparatus such as a personal computer in advance requires not only a storage apparatus having a large storage capacity enough to store adjustment parameter data for the number of the types, but also the work of management and addition of new adjustment parameter data to the storage apparatus each time a new type of endoscope emerges.

However, as described above, the endoscope system according to the present embodiment enables simple adjustment of timings for image pickup signal sampling without storing adjustment parameters for each of all of endoscopes in an adjustment apparatus and managing the adjustment parameters.

The adjustment enables automatic setting of optimum sampling timings by means of providing an adjustment instruction at the time of manufacture or repair, and thus, no variations depending on the workers occur, enabling setting of optimum sampling positions for each endoscope.

Furthermore, the endoscope system according to the present embodiment sets the content of a timing determination procedure for each endoscope, enabling setting of optimum sampling positions even if an image pickup signal from an endoscope has a waveform that is different from that of another endoscope.

Furthermore, even if the length of the signal wire is changed as a result of repair, optimum sampling positions can be set by providing an adjustment instruction.

Also, for a new endoscope, sampling timing setting and adjustment can be made merely by changing the timing determination procedure information stored in the rewritable storage section, facilitating a response to a new endoscope.

Furthermore, the endoscope system according to the present embodiment enables automatic sampling timing adjustment to be made in a site where the endoscope system is used, for example, a hospital.

The present invention is not limited to the above-described embodiment, and various modifications, alterations and the like are possible without departing from the spirit of the present invention.

What is claimed is:

1. An endoscope comprising:
   an image pickup device drive circuit configured to output a drive signal for driving an image pickup device provided in an insertion portion of the endoscope;
   a correlated double sampling circuit configured to output a post-sampling image pickup signal obtained by sampling an image pickup signal outputted from the image pickup device driven by the drive signal, via a feedthrough sampling pulse and a clamp pulse;
   a control apparatus configured to control a sampling timing of each of the feedthrough sampling pulse and the clamp pulse used in the correlated double sampling circuit, and configured to evaluate the post-sampling image pickup signal outputted from the correlated double sampling circuit; and
   a storage apparatus configured to be rewritable and to store timing information on respective timings controlled by the control apparatus, and timing determination procedure information determined by an evaluation range of the post-sampling image pickup signal based on a type of the endoscope,
   wherein the control apparatus, upon receipt of an adjustment instruction for adjustment of the respective timings of the feedthrough sampling pulse and the clamp pulse, rewrites the timing information in the storage apparatus according to a result of evaluation of a plurality of post-sampling image pickup signals obtained by shifting the respective timings based on the timing determination procedure information, the shifting of the respective timings being performed by, with timing of one of the feedthrough sampling pulse and the clamp pulse fixed, shifting timing of the other of the feedthrough sampling pulse and the clamp pulse, and then by, with the timing of the other of the feedthrough sampling pulse and the clamp pulse fixed, shifting the timing of the one of the feedthrough sampling pulse and the clamp pulse, and
   wherein the timing determination procedure information includes:
      an evaluation criterion for designating either of evaluations that each of the post-sampling image pickup signals is evaluated based on both of a noise level and an output level of the post-sampling image pickup signal and that each of the post-sampling image pickup signals is evaluated based only on an output level of the post-sampling image pickup signal;
      adjustment parameters for a range in which the respective timings are shifted and a sampling position for each of a feedthrough waveform part and an output waveform part in an image pickup signal corresponding to one pixel; and
      environment setting information at least including a set value for a light source apparatus and a gain of a circuit in the endoscope when the plurality of post-sampling image pickup signals are obtained by the control apparatus shifting the respective timings.

2. An endoscope system including an endoscope and a body apparatus to which the endoscope is connected, the endoscope system having an observation mode for observing an object and an adjustment mode for adjusting the endoscope,
   wherein the body apparatus includes an adjustment instruction inputting circuit configured such that a start of the adjustment mode is inputted via the adjustment instruction inputting circuit,
   wherein the endoscope includes:
      an image pickup device drive circuit configured to output a drive signal for driving an image pickup device provided in an insertion portion of the endoscope;
      a correlated double sampling circuit configured to output a post-sampling image pickup signal obtained by sampling an image pickup signal outputted from the image pickup device driven by the drive signal, via a feedthrough sampling pulse and a clamp pulse;
      a control apparatus configured to control a sampling timing of each of the feedthrough sampling pulse and the clamp pulse used in the correlated double sampling circuit and configured to evaluate the post-sampling image pickup signal outputted from the correlated double sampling circuit; and
      a storage apparatus configured to be rewritable and to store timing information on respective timings controlled by the control apparatus, and timing determination procedure information determined by an evaluation range of the post-sampling image pickup signal based on a type of the endoscope,
   wherein the control apparatus of the endoscope, upon receipt of an instruction to select the adjustment mode from the body apparatus, rewrites the timing information in the storage apparatus according to a result of evaluation of a plurality of post-sampling image pickup signals obtained by shifting the respective timings of the feedthrough sampling pulse and the clamp pulse based on the timing determination procedure information, the shifting of the respective timings being performed by, with timing of one of the feedthrough sampling pulse and the clamp pulse fixed, shifting timing of the other of the feedthrough sampling pulse and the clamp pulse, and then by, with the timing of the other of the feedthrough sampling pulse and the clamp pulse fixed, shifting the timing of the one of the feedthrough sampling pulse and the clamp pulse, and wherein the timing determination procedure information includes environment setting information at least including a set value for a light source apparatus and a gain of a circuit in the endoscope when the plurality of post-sampling image pickup signals are obtained by the control apparatus shifting the respective timings.

* * * * *